United States Patent [19]

von Bittera et al.

[11] Patent Number: 4,661,099

[45] Date of Patent: Apr. 28, 1987

[54] SELF-ADHESIVE SHEET-LIKE STRUCTURES, PROCESS FOR THEIR PREPARATION AND THEIR USE

[75] Inventors: Miklos von Bittera, Leverkusen; Dietmar Schäpel, Cologne; Ulrich von Gizycki, Leverkusen; Roland Rupp, Leichlingen, all of Fed. Rep. of Germany

[73] Assignee: Bayer Aktiengesellschaft, Leverkusen, Fed. Rep. of Germany

[21] Appl. No.: 669,402

[22] Filed: Nov. 8, 1984

[30] Foreign Application Priority Data

Nov. 17, 1983 [DE] Fed. Rep. of Germany ....... 3341555

[51] Int. Cl.⁴ .................. A61F 13/02; A61L 15/06; C08K 5/06; C08L 75/04
[52] U.S. Cl. .................... 604/290; 128/156; 604/307; 522/146; 427/208.2; 428/261; 428/334; 428/355; 523/111; 524/724; 524/762; 524/874; 524/875
[58] Field of Search ............... 523/111; 524/762, 724, 524/874, 875, 377, 590; 604/307, 290, 304; 128/156; 428/334, 261, 355

[56] References Cited

U.S. PATENT DOCUMENTS

| | | | |
|---|---|---|---|
| 4,404,296 | 9/1983 | Schäpel | 523/105 |
| 4,456,642 | 6/1984 | Bürgdorfer et al. | 428/68 |
| 4,505,976 | 3/1985 | Doehnert | 523/111 |
| 4,517,326 | 5/1985 | Cordts | 524/377 |
| 4,548,845 | 10/1985 | Parsons | 524/377 |

FOREIGN PATENT DOCUMENTS 0057839  8/1982  European Pat. Off.
2128408  10/1972  France .
2226453  11/1974  France .
2237946  2/1975  France .

*Primary Examiner*—C. Warren Ivy
*Attorney, Agent, or Firm*—Gene Harsh; Lawrence S. Pope

[57] ABSTRACT

The present disclosure is concerned with self-adhesive sheet-like structures made by adhering an adhesive polyurethane gel material to a supporting substrate and the utilization of such structures in the medical field to adhere materials such as plasters, wound dressings and appliances to the human body, and in other fields to connect articles, such as the parts of a fractured or cracked object, to one another by means of an adhesive bond. The gel is formed by immobilizing a high molecular weight polymeric polyol in the matrix of a covalently crosslinked polyurethane which is prepared by reacting polyisocyanates having an isocyanate functionality of at least 2 with higher molecular weight polyhydroxyl compounds having a hydroxyl functionality of at least 3. These reactants are selected in accordance with the following formula which relates the isocyanate number, K, (isocyanate to hydroxyl equivalents ratio times 100) to the average functionalities of the polyisocyanates ($F_I$) and of the polyhydroxyl compounds ($F_P$) as follows:

$$K = \frac{300 \pm X}{(F_I \cdot F_P) - 1} + 7$$

wherein X is less than or equal to 120. These reactants are also selected to give a weight ratio of matrix to immobilized polymeric polyol of between about 15:85 and 62:38.

33 Claims, No Drawings

SELF-ADHESIVE SHEET-LIKE STRUCTURES, PROCESS FOR THEIR PREPARATION AND THEIR USE

FIELD OF THE INVENTION

The present invention relates to novel self-adhesive sheet-like structures comprising at least one support layer and at least one adhesive layer based on polyurethane gel. The sheet-like structures can be obtained by coating a very wide variety of support materials with a reaction mixture which comprises diisocyanates and/or polyisocyanates and an excess amount of high molecular weight polyols, followed by curing, and they can be used, for example, for medical purposes as an adhesive plaster tolerated by the skin, or for industrial applications as an adhesive.

BACKGROUND OF THE INVENTION

Various embodiments of self-adhesive sheet-like structures are known, such as, for example, medical plasters. Skin plasters for medical purposes customarily have adhesive surfaces based on rubber resins or polyacrylates. The plasters having rubber adhesive surfaces have the disadvantage that residues, which are difficult to remove, remain on the skin when these plasters are removed again. In addition, these plasters frequently lead to skin irritation. The disadvantages of plasters having adhesive surfaces based on polyacrylates are the occasionally occurring skin reddening, which may progress to skin irritation, and the skin softening processes which are generally seen when there is inadequate access for air. These disadvantages appear particularly intense when polyacrylate adhesive surfaces remain on the skin for longer than one day, and when the surface covered by the adhesive is relatively large in extent.

Self-adhesive sheet-like structures which are used for industrial purposes and whose adhesive effect is based on polyvinyl chloride (PVC), (PVC being used either as an adhesive coating on a support material or as a self-adhesive film) have the disadvantage that an adequate adhesive effect is only achieved on smooth and even substrates. In addition, some of the low molecular weight plasticizers generally contained in PVC act, because of their chemical structure, as solvents and/or they are able to migrate into the substrates.

It has now been found that self-adhesive sheet-like structures which adhere well even to rough and uneven surfaces, can be removed again leaving virtually no residues and, in addition, are tolerated by the skin, are obtained by coating any desired support materials with a polyurethane reaction mixture which cures with the formation of a highly elastic gel of firm structure. Gels similar to those used in the present invention are disclosed in U.S. Pat. No. 4,456,642 including some gels which have a tacky gelatinous consistency. However, the disclosure does not teach that gels within its broad teaching could have utility as adhesive materials nor does it teach how to select gels within its broad teachings which have this property.

BRIEF DESCRIPTION OF THE INVENTION

Thus, the invention relates to self-adhesive sheet-like structures containing at least one support layer and at least one adhesive layer, one of the two surfaces of the sheet-like structure being at least partially covered with an adhesive layer, characterized in that this adhesive layer is a gel which contains (A) about 15–62% by weight, preferably about 20–57% by weight, particularly preferably about 25–47% by weight, relative to the total of (A) and (B), of a covalently crosslinked polyurethane as the high molecular weight matrix and (B) about 85–38% by weight, preferably about 80–43% by weight, particularly preferably about 75–53% by weight, relative to the total of (A) and (B), of one or more polyhydroxy compounds which are immobilized in the matrix by intermolecular forces and have an average molecular weight between about 1,000 and 12,000, preferably between about 1,500 and 8,000, particularly preferably between about 2,000 and 6,000, and an average OH value between about 20 and 112, preferably between about 25 and 84, particularly preferably between about 28 and 56, as a liquid dispersing agent, the dispersing agent '15 being essentially free of hydroxy compounds having a molecular weight below about 800, preferably below about 1,000, particularly preferably below about 1,500, and, where appropriate, (C) 0–100% by weight, relative to the total of (A) and (B), of fillers and/or additives and which can be obtained by reaction of a mixture of (a) one or more polyisocyanates, (b) one or more polyhydroxy compounds having an average molecular weight between about 1,000 and 12,000 and an average OH value between about 20 and 112, (c) where appropriate, catalysts for the reaction between isocyanate and hydroxyl groups, preferably between about 0.05 and 10 weight % of the total weight of the gel, and, where appropriate, (d) fillers and additives which are known per se from polyurethane chemistry, this mixture being essentially free of hydroxy compounds having a molecular weight below about 800, the average isocyanate functionality of the polyisocyanates ($F_I$) being preferably between 2 and 4, the average hydroxyl functionality of the polyhydroxy compounds ($F_P$) being at least 3, and the isocyanate number (K) obeying the formula $$K = \frac{300 \pm X}{(F_I \cdot F_P) - 1} + 7$$

in which $X \leq 120$, preferably $X \leq 100$, and particularly preferably $X \leq 90$, and in which the isocyanate number (K) is the ratio of isocyanate (NCO) to hydroxyl (OH) equivalents in the reaction mixture multiplied by 100.

The indicated average figures for molecular weight and OH value are to be understood to be number averages.

The invention also relates to a process for the preparation of self-adhesive sheet-like structures based on support materials coated with polyurethane gel: the process is characterized in that the reaction mixtures which are capable of gel formation and are defined above are applied to the surface of a support material by a direct or reverse process by pouring, knife coating or spraying, the surface being only partly covered by the gel-forming reaction mixture where appropriate.

Finally, the invention also relates to the use of the self-adhesive sheet-like structures in medicine, in particular as adhesive or wound plasters, dressings or gauze bandages.

DETAILED DESCRIPTION OF THE INVENTION

The sheet-like structures according to the invention can be prepared from the starting compounds which are known per se from polyurethane chemistry by techniques which are broadly described in, for example, DE-OS (German Published Specification) 3,103,499, DE-OS (German Published Specification) 3,103,500 and U.S. Pat. No. 4,404,296, incorporated herein by reference. However, it is essential that, in the selection of the gel-forming components, the conditions defined above are observed, since otherwise non-adhesive, elastic gels are obtained in place of self-adhesive gel layers.

Polyhydroxy compounds preferred according to the invention are polyether-polyols as are detailed in the above-mentioned German Offenlegungsschriften (German Published Specifications) and U.S. Pat. No. 4,404,296. Both (cyclo)aliphatic and aromatic isocyanates are suitable as the polyisocyanate component. Preferred (cyclo)aliphatic polyisocyanates are 1,6-hexamethylene diisocyanate and its biurets and trimers, and hydrogenated diphenylmethane diisocyanate ("MDI") types. Preferred aromatic polyisocyanates are those which are obtained by distillation, such as MDI mixtures of 4,4'- and 2,4'-isomers or 4,4'-MDI, and toluylene diisocyanate ("TDI") types. The TDI types can also contain more highly functionalized fractions based on modifications, such as biuretization or trimerization.

In a preferred manner according to the invention, the starting components are selected such that, in the gel-forming reaction mixture, the average NCO functionality is between 2 and 4, the average polyol functionality is between 3 and 6, and the isocyanate number (K) is between about 15 and 70, preferably between about 18 and 55, and particularly preferably between about 20 and 45.

The adhesive layers consisting of polyurethane gel on the sheet-like structures according to the invention can, where desired, contain additives known per se from polyurethane chemistry, such as, for example, fillers and short inorganic- or organic-based fibers, metal pigments, water-binding agents, surface-active substances or liquid extenders, such as substances having a boiling point above 150° C.

Examples of inorganic fillers which may be mentioned are barytes, chalk, gypsum, kieserite, soda, titanium dioxide, cerium oxide, quartz sand, kaolin, carbon black and hollow glass microspheres.

Examples of organic fillers which can be used are powders based on polystyrene, polyvinyl chloride, urea-formaldehyde and polyhydrazodicarbonamide (for example from hydrazine and toluylene diisocyanate).

Examples of suitable short fibers are glass fibers 0.1–1 mm in length, or fibers of organic origin such as, for example, polyester or nylon fibers. Metal powders such as, for example, iron or copper powder, can likewise be used in the gel formation. In order to confer the desired coloration to the gels according to the invention, it is possible to use organic- or inorganic-based dyestuffs or coloring pigments known per se for the coloring of polyurethanes, such as, for example, iron oxide or chromium oxide pigments, or phthalocyanine- or monoazo-based pigments. Zeolites are the preferred water-binding agents. Examples of surface-active substances which may be mentioned are powdered cellulose, active charcoal, silica products and chrysotile asbestos.

Examples of suitable liquid extenders are alkyl-, alkoxy- or halogen-substituted aromatic compounds, such as dodecylbenzene, m-dipropoxybenzene or o-dichlorobenzene, halogenated aliphatic compounds, such as chlorinated paraffins, organic carbonates, such as propylene carbonate, carboxylic esters, such as dioctyl phthalate, ethyl stearate, lauric acid hexyl ester, isopropyl myristate, isopropyl palmitate or dodecylsulphonic esters or organic phosphorus compounds, such as tricresyl phosphate. In addition, it is also possible to use as liquid extenders high molecular weight polyols whose hydroxyl groups have been etherified, esterified or urethanized, or also silicone oils or paraffin oils.

The content of fillers and extenders in the gel layer can amount to up to about 50% by weight relative to the total weight of the gel.

Where appropriate for modification of the adhesion properties of the gel layer, it is possible to add polymeric vinyl compounds, polyacrylates and other copolymers customary in adhesive technology, as well as adhesives based on natural materials, up to a content of about 10% by weight, relative to the weight of the gel composition.

The thickness of the gel layer can be between, for example, about 0.001 mm and 5 mm, preferably between about 0.01 mm and 2 mm, and particularly preferably between about 0.1 mm and 1 mm.

A very wide variety of origins is possible for the support materials contained in the self-adhesive sheet-like structures according to the invention, that is to say materials based on natural, cellulosic or synthetic raw materials and of organic or inorganic origin can be used. For example, it is possible to employ plastic films and metal foils, mats, bonded fiber webs, and knitted or woven fabrics of organic or inorganic fibers, paper, board, wood, leather and plastic foam sheeting, or combinations of these support materials. Sheet-like structures which are permeable to air and moisture are preferred for medical applications, for example microporous and macroporous plastic films, elastic textile support materials, in particular stretch fabric, and gauze bandages.

The gels contained in the sheet-like structures according to the invention can be prepared by various means.

For example, it is possible to use a one-shot process or a prepolymer process. In the one-shot process, all the components, that is to say polyols, diisocyanates and/or polyisocyanates, the catalysts accelerating the isocyanate polyaddition reaction and, where appropriate, fillers and additives, are together placed in one vessel and thoroughly mixed with one another.

In the prepolymer process, there are two possible procedures. Either first an isocyanate prepolymer is prepared by reacting an appropriate fraction of the amount of polyol with the total amount of isocyanate intended for gel formation, and then the remaining amount of polyol and, where appropriate, fillers and additives are added to the resulting prepolymer, with thorough mixing: or the entire amount of polyol intended for gel formation is reacted with a portion of the amount of isocyanate to give a hydroxy prepolymer, and then the remaining amount of isocyanate is mixed in.

A particularly advantageous procedure according to the invention is a variant of the one-shot process and of the hydroxy prepolymer process. In this, the polyol or mixture of polyols, where appropriate the fillers and additives, the catalyst and two different diisocyanates are put together in one shot and mixed thoroughly, one diisocyanate being aromatic and one diisocyanate being aliphatic. It can be assumed that, due to the great difference in reactivity of the two diisocyanates, first a hydroxy prepolymer is produced, which then, within minutes, reacts with the other diisocyanate to form a gel.

In these procedures, the transport, dosage and mixing of the individual components or mixtures of components can be carried out with devices known per se to the expert in polyurethane chemistry.

The sheet-like structures according to the invention can be produced continuously or discontinuously. The procedure depends on the sheet-like structures which it is intended to provide with an adhesive layer. When support material which has already been cut to shape is supplied, a discontinuous procedure is frequently advantageous. For coating support materials which are continuous, for example in the form of rolls, a continuous procedure is advisable. This can entail the gel-like adhesive layer being applied to the support material either directly or by a reverse process. In the processes mentioned, the reaction mixture which is capable of gelling can also be knife-coated or spray-coated before it congeals due to the reaction. The spray process makes it possible, for example, for wide-mesh fabrics to be straightforwardly coated in dot form.

Preferably, the sheet-like structures according to the invention are exposed to gamma radiation. By means of this after-treatment the adhesion capacity of the gel layer is improved, i.e there is stronger adhesion to substrates of any kind.

An essential advantage of the sheet-like structures according to the invention when used as medical plasters is that they are well tolerated by the skin. No softening, or other damage to the skin caused by impermeability to air or water vapor, is found. Moreover, as plasters, the sheet-like structures according to the invention can be detached again from the skin by a gentle tug, with no epilation occurring, and they leave virtually no residue.

Thus, a particular embodiment of the sheet-like structures according to the invention is represented by wound dressings which consist of a support material having a self-adhesive polyurethane gel layer, on the center of which is located a pad for the wound, in order to enclose the wound on all sides. In this context, the support material can consist of, for example, a plastic film based on, for example, polyurethane (PUR) or PVC, a plastic foam sheeting based on, for example, PVC, PUR or polyethylene or, preferably, bonded fiber textiles based on, for example, viscose fibers, and fabrics based on, for example, rayon, or stretch knitted fabrics based on, for example, PUR/nylon blended yarns. It is possible to use as the absorbent central pad for the wound those materials known to be tolerated by wounds, such as, for example, cotton gauze, PUR plastic foam sheeting or viscose textile webs having a fabric structure. However, combinations of a wound pad based on, for example, cotton gauze or viscose textile webs, which is, where appropriate, aluminized, and an absorbent layer based on, for example, cellulose, viscose or viscose/ cotton (25:75) blends are preferred. The pad for the wound can also consist of a chemically crosslinked gel which absorbs discharge from the wound, for example a PUR gel according to European Patent A 0,057,839, the gel being optionally expanded to increase its absorbence, thus being an expanded gel. Possible applications of wound dressings of this type are for caring for wounds which are dry or discharging slightly, and, in a special embodiment, that is to say with a soft central cushion pad, also as a dressing for the eyes or a dressing for corns.

It is possible to produce, as a variant of the wound dressing which is suitable for caring for minor wounds, first-aid dressings which can consist of, for example, the same material combinations as the wound dressings, but have, in place of the central pad for the wound, a continuous pad for the wound.

A further embodiment of the sheet-like structures according to the invention is represented by inelastic (inextensible) and elastic bandages based on cotton or cotton/PUR or cotton/nylon blended yarns, the bandages being provided with the self-adhesive non-slip PUR gel by wetting or coating. Bandages of these types can be used for compression and support dressings and as sports strapping, advantageously on joints or tapering parts of the body. The extensibility required for each elastic bandage is normally achieved not only by the type of yarn but, in particular, by the technique of weaving or knitting the bandages, which are then provided with the gel.

The fixing tapes which are used for a variety of purposes in medical applications consist, according to the invention, of a support material which is provided with an adhesive layer of polyurethane gel. Examples of support materials which can be used for this are plastic films based on, for example PVC or PUR, plastic foam sheeting based on, for example, polyethylene, PVC or PUR, bonded fiber textiles based on, for example, viscose, fabrics based on, for example, rayon, cotton or, preferably, stretch knitted fabrics based on, for example, PUR/nylon blended yarns. By punching suitable rows of holes or serrated edges, the fixing tapes can be designed in a form which can be torn by hand. The fixing tapes according to the invention can be used for attaching, for example, tubes, catheters, measuring probes, dressings, ointment compresses, wound compresses, eye compresses or navel compresses.

An embodiment of a skin plaster containing an active compound which is suitable for transdermal administration of the active compound consists, according to the invention, of a support material which is provided with an adhesive layer of polyurethane gel, on the center of which is located a pad containing active compound. Between this support material coated with gel and this pad containing active compound, there is a separating layer which seals off diffusion of the particular active compound and is composed of, for example, aluminum foil, which is optionally provided on the side facing the pad containing the active compound with a sealable film, for example based on EVA (ethylene vinyl acetate), in order to be able to lock the active compound in tightly by means of a sealable covering layer. It is possible to use as the support material for the pad containing active compound, depending on the purpose for which it is used and the type of active compound, gel-like compositions based on, for example, polyurethane, PVC or polyisobutylene, and bonded fiber webs based on, for example, viscose. The support material, which has the adhesive gel layer, for the plaster containing active compound can consist of the same materials as are described above for the case of wound dressings.

It is possible for the various plasters, bandages and dressings to be coated with the gel which produces the adhesive effect either throughout or only partially: they can be microporous or macroporous or even perforated. Thus, for example, it is possible for gauze bandages or other inelastic or elastic bandages to be provided with the self-adhesive gel composition in only small areas (for example on the longitudinal margins, in the form of strips at right angles to the direction of winding or as dots), for example to achieve a non-slip effect.

A further advantage of the sheet-like structures according to the invention is their ability to adhere even to rough, uneven and highly contoured substrates. For this reason, there are industrial applications of the sheet-like structures according to the invention in many embodiments, for example as adhesive surfaces for notice and information boards: as material for temporary repair of cracked materials or broken parts: as a fixing aid for promotional material: in the form of adhesive films or fabrics which can be cut to produce modeling material for children; as a surface for insects to adhere to; as adhesive labels; as an adhesive surface for envelopes: as a protective film on car windows to counter the deposition of layers of ice at night.

The examples which follow illustrate the present invention.

Quantitative data are to be understood to be percentages by weight or parts by weight unless otherwise indicated.

The following polyisocyanates and polyols were used in the examples:

Polyisocyanate 1: 1,6-Hexamethylene diisocyanate.

Polyisocyanate 2: Commercial 1,6-hexamethylene diisocyanate which has been biuretized and has an average NCO functionality of 3.6, an NCO content of 21% and an average molecular weight (number average) of about 700 (Desmodur ®N of Bayer AG)

Polyisocyanate 3: Mixture of isomers comprising 80% 2,4- and 20% 2,6-toluylene diisocyanate Polyisocyanate 4: 4,4'-Diisocyanatodiphenylmethane liquefied by prepolymerization with tripropylene glycol; average NCO functionality: 2.05: NCO content: 23%

Polyisocyanate 5: 1,6-Hexamethylene diisocyanate modified by trimerization, average NCO functionality: 3.4: NCO content: 21.5%: average molecular weight (number average)=about 675.

The polyether-polyols used in the examples are compiled in the table below.

They were prepared by addition, in a manner known per se, of propylene oxide, and, where appropriate, ethylene oxide, onto the starter molecules indicated.

| Polyol No. | Propylene oxide % | Ethylene oxide % | Starter molecule | OH value | OH functionality |
| --- | --- | --- | --- | --- | --- |
| 1 | 80 | 20 | PET | 36 | 4 |
| 2 | 100 | — | Sorbitol | 46 | 6 |
| 3 | 73 | 27 | Sorbitol | 30 | 6 |
| 4 | 45 | 55 | TMP | 56 | 3 |
| 5 | 100 | — | PET | 72 | 4 |
| 6 | 100 | — | TMP | 56 | 3 |
| 7 | 90 | 10 | Sorbitol | 83 | 6 |
| 8 | 100 | — | EDA | 61 | 4 |
| 9 | 83 | 17 | TMP | 35 | 3 |
| 10 | 100 | — | PET | 45 | 4 |

PET = pentaerythritol
TMP = trimethylolpropane
EDA = ethylenediamine

EXAMPLE 1

100 parts of polyether 1, 6.1 parts of polyisocyanate 4 and 0.6 parts of dibutyltin dilaurate are, within one minute, thoroughly mixed and poured out onto silicone-treated paper to give a layer 0.5 mm thick. After 10 minutes, the gel-forming reaction starts and the viscosity of the reaction mixture slowly increases. An elastic knitted fabric based on nylon/polyurethane fibers is applied, without creases, to the highly viscous film of the reaction mixture. After 20 minutes, the mixture has congealed to form a gel. The gel-coated stretch material is divided into pieces each 12×10 cm in size, and pieces of wound gauze each 4×6 cm in size are applied to the gel-coated side in such a manner that an adhesive layer of gel, which is 3 cm wide, is retained around the periphery of each. A wound dressing of this type is suitable for caring for wounds on parts of the body which are subject to extensive movement, such as, for example, joints.

EXAMPLE 2

100 parts of polyether 3, 3.9 parts of polyisocyanate 4 and 1 part of dibutyltin dilaurate are, within one minute, thoroughly mixed and poured out onto silicone-treated paper to give a layer 0.5 mm thick. After 10 minutes, the gel-forming reaction starts, and the viscosity of the reaction mixture slowly increases. A bonded fiber textile based on viscose is applied, without creases, to the highly viscous film of the reaction mixture.

After 20 minutes, the mixture has congealed to form a gel. The gel-coated bonded fiber textile is divided into pieces each 8×10 cm in size, and pieces of wound gauze, which are each 4×6 cm in size, are applied to the gel-coated side in such a manner that an adhesive layer of gel, which is 2 cm wide, is retained around the periphery of each.

The resulting wound dressing is suitable for caring for wounds which are dry or discharging slightly.

EXAMPLE 3

100 parts of polyether 4, 9.8 parts of polyisocyanate 4 and 2 parts of dibutyltin dilaurate are, within one minute, thoroughly mixed and spread on a Teflon plate to form a layer 0.1 mm thick. After 10 minutes, the gel-forming reaction starts and the viscosity of the reaction mixture slowly increases. An elastic knitted fabric based on nylon/polyurethane fibers is applied, without creases, to the highly viscous film of the reaction mixture. After 20 minutes, the mixture has congealed to form a gel. The gel-coated stretch material is divided into strips 8 cm wide. Strips of viscose textile web (with a fabric structure) which are each 2.6 cm wide are glued onto the center of the gel-coated side of the strips, in a longitudinal direction in such a manner that a zone of adhesive gel, which is 2.7 cm wide on each side, is retained in the longitudinal direction on the borders.

The resulting strips can be divided across in pieces which are 1 to 3 cm wide and which then can be used as first-aid dressings for caring for minor wounds.

EXAMPLE 4

100 parts of polyether 2, 5.3 parts of polyisocyanate 4 and 1 part of dibutyltin dilaurate are, within one minute, thoroughly mixed and, using a spray gun, sprayed onto an elastic bandage (cotton weft threads, crimped nylon warp threads), the amount of gel composition applied being 35 parts per square meter. Coagulation to form a gel is complete after 10 minutes.

The resulting bandage which has been sprayed with gel is suitable for applying dressings to tapering parts of the body, since the individual layers of the bandage adhere very well to one another, and thus do not slip during movement.

EXAMPLE 5

A mixture of 100 parts of polyether 1, 3.6 parts of polyisocyanate 5 and 3.parts of dibutyltin dilaurate is used to coat, by the procedure described in Example 1, an elastic knitted fabric based on nylon (84%) and polyurethane (16%).

The 3 cm-wide strips obtained by dividing the coated stretch knitted fabric are suitable for immobilizing catheters and tubes as well as emergency wound gauze dressings.

EXAMPLE 6

The process is carried out exactly as in Example 5 but, in place of the combination of polyether 1 and polyisocyanate 5, the combinations of polyethers and polyisocyanates listed below are used:

| 100 parts of polyether | are mixed with the following parts by weight of polyisocyanates |
|---|---|
| No. 2 | 4.3 parts of polyisocyanate 5 |
| No. 4 | 6.6 parts of polyisocyanate 5 |
| No. 5 | 8.5 parts of polyisocyanate 5 |
| No. 6 | 7.6 parts of polyisocyanate 5 |
| No. 1 | 3.6 parts of polyisocyanate 2 |
| No. 2 | 4.1 parts of polyisocyanate 2 |
| No. 3 | 2.46 parts of polyisocyanate 2 |
| No. 4 | 5.2 parts of polyisocyanate 2 |
| No. 7 | 5.0 parts of polyisocyanate 2 |
| No. 1 | 2.9 parts of polyisocyanate 1 |
| No. 3 | 1.8 parts of polyisocyanate 1 |
| No. 9 | 4.15 parts of polyisocyanate 2 |

EXAMPLE 7

A mixture of 100 parts of polyether 7, 7.56 parts of polyisocyanate 4 and 2 parts of dibutyltin dilaurate is, within one minute, thoroughly mixed and spread on a Teflon plate to give a film 0.3 mm thick. A bonded fiber textile based on viscose is laid, without creases, onto the film which is becoming highly viscous due to the reaction. After gel formation is complete, the bonded fiber fabric which has been provided with a film of gel is divided into strips 2 cm wide.

Strips of this type are suitable for attaching information sheets or advertising posters to shop windows.

EXAMPLE 8

The process is carried out exactly as in Example 7, but in place of the combination of polyether 7 and polyisocyanate 4, the combinations of polyethers and polyisocyanates listed below are used:

| 100 parts of polyether | are mixed with the following parts of polyisocyanate |
|---|---|
| No. 8 | 9.9 parts of polyisocyanate 4 |
| No. 1 | 3.14 parts of polyisocyanate 3 |
| No. 4 | 5.15 parts of polyisocyanate 3 |
| No. 10 | 8.8 parts of polyisocyanate 4 |

EXAMPLE 9

100 parts of polyether 2, 15 parts of an oil based on polydimethylsiloxane (Baysilone oil M 5000, Bayer AG) with a viscosity of 5000 mm$^2$/sec at 25° C., 5 parts of polyisocyanate 4 and 0.1 part of dibutyltin dilaurate are thoroughly mixed together, poured onto a Teflon plate and spread to form a layer 0.1 mm thick.

The viscosity has increased greatly after 10 minutes An extensible knitted fabric based on nylon/ polyurethane is laid onto the highly viscous reaction mixture. After 30 minutes, the gel-coated knitted fabric is detached from the plate and cut into strips 3 cm wide. Strips of this type can be used as fixing tapes for medical applications, such as, for example, for affixing dressings.

EXAMPLE 10

The process is carried out exactly as in Example 9 but, in place of the oil based on polydimethylsiloxane, an oil based on polymeric methylphenylsiloxane (Baysilone oil PH 300, Bayer AG) with a viscosity of 300 mm$^2$/sec at 25° C. is used.

The resulting gel-coated strips can likewise be used as fixing tapes for medical applications.

The adhesion capacity of sheets according to the invention may be determined by the following method: a gel-coated strip (125 mm×25 mm) is pressed onto a clean smooth plate of VA-steel with a pressure of 7,5 Newton. Then the strip is detached from the steel surface at a rate of 100 mm/min. The force which has to be used to detach the specimen from the substrate is plotted by means of an x-y- recorder against the distance which has been detached. From the force/length diagram obtained the average force $\overline{F}$ is determined which has to be applied to detach the first 75 mm of the test specimen. $\overline{F}$ should be at least 0,5 N, preferably at least 1, 0 N, more preferably at least 2 N for sheet like structures according to the invention.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An adhesive sheet structure comprising at least one support layer and at least one adhesive layer, one of the two surfaces of the structure being at least partially covered with an adhesive layer which is a gel comprising
    (A) about 15–62% by weight, relative to the total of (A) and (B), of a covalently crosslinked polyurethane as a high molecular weight matrix and
    (B) about 85–38% by weight, relative to the total of (A) and (B), of one or more polyhydroxy compounds which are immobilized in said matrix by van der Walls' forces, have an average molecular weights between about 1,000 and 12,000, and average OH values between about 20 and 112 and serve as a liquid dispersing agent, this dispersing agent being essentially free of hydroxy compounds having a molecular weight below about 800, and
    (C) 0–100% by weight, relative to the total of (A) and (B), of fillers and/or additives, said gel being obtained by the reaction of a mixture of
        (a) one or more polyisocyanates, and
        (b) one or more polyhydroxy compounds having average molecular weight between about 1,000 and 12,000 and an average 1 value between about 20 and 112, which mixture may also include
(c) catalysts for the reaction between isocyanate and hydroxyl groups and
(d) fillers and additives which are known per se from polyurethane chemistry, this mixture being essentially free of hydroxy compounds having a molecular weight below about 800, the average functionality of the polyisocyanates ($F_I$) being at least 2, the average functionality of the polyhydroxy compounds ($F_P$) being at least 3, and the isocyanate number (K) obeying the formula $$K = \frac{300 \pm X}{(F_I \cdot F_P) - 1} + 7$$

in which $X \leq 120$, said adhesive sheet structure requiring an average force ($\overline{F}$) of at least about 0.5 Newton for detachment of 75 mm of a 125 mm long and 25 mm wide strip initially adhered to a smooth steel plate with a pressing force of 7.5 Newton when the rate of detachment is 100 mm per minute.

2. The adhesive sheet structure of claim 1 wherein X is less than or equal to 100.

3. The adhesive sheet structure of claim 2 wherein X is less than or equal to 90.

4. The adhesive sheet of claim 1 or claim 2 or claim 3 wherein the average functionality ($F_I$) of the polyisocyanates is between 2 and 4 and the average functionality ($F_P$) of the polyhydroxy compounds is between about 3 and 6.

5. The adhesive sheet structure of claim 1, wherein the gel contains
(A) about 20-57% by weight, relative to the total of (A) and (B), of the covalently crosslinked polyurethane and
(B) about 80-43% by weight, relative to the total of (A) and (B), of the liquid dispersing agent.

6. The adhesive sheet structure of claim 5, wherein the gel contains
(A) about 25-57% by weight of the covalently crosslinked polyurethane and
(B) 75-53% by weight of the liquid dispersing agent.

7. The adhesive sheet structure of claim 1 or 2 or 3 or 5, wherein the polyhydroxy compounds of the liquid dispersing agent have an average molecular weight between about 1,500 and 8,000.

8. The adhesive sheet structure of claim 7, wherein the polyhydroxy compounds of the liquid dispersing agent have an average OH value between about 25 and 84.

9. The adhesive sheet structure of claim 7, wherein the liquid dispersing agent is essentially free of hydroxy compounds having a molecular weight below about 1,000.

10. The adhesive sheet structure of claim 9, wherein the liquid dispersing agent is essentially free of hydroxy compounds having molecular weight below about 1,200.

11. The adhesive sheet structure of claim 1 or 7, wherein the isocyanate number (K) is between about 15 and 70.

12. The adhesive sheet structure of claim 11 wherein the isocyanate number (K) is between about 18 and 55.

13. The adhesive sheet structure of claim 12 wherein the isocyanate number (K) is between 20 and 45.

14. A bandage material which comprises the adhesive sheet structure of claim 1 and a medicinally effective material which is on the same surface of the support layer as the adhesive layer gel.

15. The bandage material of claim 14 wherein the medicinally effective material is a plaster.

16. The bandage material of claim 14 wherein the medicinally effective material is a wound dressing.

17. The sheet-like structure of claim 1 wherein the support layer is elastic and said structure is adapted to being used as an elastic support bandage.

18. The adhesive sheet structure of claim 1 in a physical form adapted to use as an inelastic support bandage.

19. A narrow tape material adapted to fixing medical appliances to the human body comprising the adhesive sheet structure of claim 1 in the form of an elongated strip.

20. A process for the production of the adhesive sheet structures of claim 1, comprising reacting a mixture of
(a) one or more polyisocyanates, and
(b) one or more polyhydroxy compounds having an average molecular weight between about 1,000 and 12,000, and an average OH value between about 20 and 112, which mixture may also include
(c) catalysts for the reaction between isocyanate and hydroxyl groups and
(d) fillers and additives known per se from polyurethane chemistry, this mixture being essentially free of hydroxy compounds having a molecular weight below about 800, the average functionality of the polyisocyanates ($F_I$) being at least about 2, the average functionality of the polyhydroxy compounds ($F_P$) being at least 3, and the isocyanate number (K) obeying the formula $$K = \frac{300 \pm X}{(F_I \cdot F_P) - 1} + 7$$

in which $X \leq 120$, to form a gel and during or after completion of the gel-forming reaction, applying the gel to at least part of the surface of a support material, said mixture being selected such that a strip of the adhesive sheet structure 125 mm long and 25 mm wide will require an average force ($\overline{F}$) at least about 0.5 Newton to detach 75 mm of length at a rate of 100 mm per minute after being adhered to a smooth steel plate with a pressing force of 7.5 Newton.

21. The process of claim 20 wherein X is less than or equal to 100.

22. The process of claim 21 wherein X is less than or equal to 90.

23. The process of claim 20 or 21 or 22 wherein the average functionality ($F_I$) of the polyisocyanate is between 2 and 4 and the average functionality ($F_P$) of the polyhydroxy compounds is between about 3 and 6.

24. A process of fixing a medical appliance to a human body comprising
(a) preparing an adhesive sheet structure in accordance with claim 20,
(b) configuring said structure into one or more elongated strips, and
(c) contacting the portion of the human body to which attachment of the medical appliance is desired with the adhesive layer gel of said structure, and
(d) securing said medical appliance to said portion by either interposing it between the portion and the structure or by attaching it to the structure by mechanical or adhesive means.

25. A process for securing a medicinally effective material to a portion of a human body comprising
(a) preparing an adhesive sheet structure in accordance with claim 20, and
(b) adhering the medicinally effective material to said portion by either attaching it to the structure or interposing it between said structure and said portion and contacting said portion with the adhesive layer gel of said structure in a manner which brings said medicinally effective material into contact with said portion of the human body.

26. The process of claim 25 wherein the medicinally effective material is a wound dressing.

27. The process of claim 25 wherein the medicinally effective material is a medical plaster.

28. The adhesive sheet structure of claim 1 wherein the adhesive layer has a thickness of between about 0.001 and 5 mm.

29. The adhesive sheet structure of claim 1 wherein the adhesive layer has a thickness of at least about 0.1 mm.

30. The process of claim 20 wherein the gel applied to the support material has a thickness of between about 0.001 and 5 mm.

31. The process of claim 30 wherein the gel applied to the support material has a thickness of at least about 0.1 mm.

32. The adhesive sheet structure of claim 1 wherein the adhesiveness as measured by $\bar{F}$ is at least 1.0 Newton.

33. The adhesive sheet structure of claim 32 wherein the adhesiveness as measured by $\bar{F}$ is at least 2 Newton.

* * * * *